United States Patent
Franck

(10) Patent No.: US 8,855,324 B2
(45) Date of Patent: Oct. 7, 2014

(54) SYSTEMS, METHODS, AND ARTICLE OF MANUFACTURE FOR CONFIGURING A HEARING PROSTHESIS

(75) Inventor: Kevin Franck, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 357 days.

(21) Appl. No.: 13/171,570

(22) Filed: Jun. 29, 2011

(65) Prior Publication Data

US 2013/0004000 A1    Jan. 3, 2013

(51) Int. Cl.
*H04R 29/00* (2006.01)
*H04R 25/00* (2006.01)

(52) U.S. Cl.
CPC .......... *H04R 25/70* (2013.01); *H04R 2225/39* (2013.01)
USPC .............. 381/60; 381/312; 381/314; 381/315

(58) Field of Classification Search
USPC .................................. 381/60, 312, 314, 315
See application file for complete search history.

(56) References Cited

U.S. PATENT DOCUMENTS

| 7,885,416 B2* | 2/2011 | Chalupper et al. .............. 381/60 |
| 2004/0037442 A1 | 2/2004 | Nielsen et al. |
| 2004/0057591 A1 | 3/2004 | Beck et al. |
| 2005/0169492 A1 | 8/2005 | Topholm |

FOREIGN PATENT DOCUMENTS

EP    0823829 A2    2/1998

OTHER PUBLICATIONS

International Search Report and Written Opinion for PCT/IB201/053324 dated Feb. 27, 2013.

* cited by examiner

*Primary Examiner* — Davetta W Goins
*Assistant Examiner* — Amir Etesam
(74) *Attorney, Agent, or Firm* — McDonnell Boehnen Hulbert & Berghoff LLP

(57) ABSTRACT

The present application discloses systems and methods for determining one or more configuration settings for a first hearing prosthesis based on configuration data associated with a second hearing prosthesis. In some embodiments, determining the one or more configuration settings for the first hearing prosthesis may include determining an acoustic operating range associated with the first hearing prosthesis based on whether a configured gain at one or more frequencies for the second hearing prosthesis meets or exceeds a target gain at the one or more frequencies. Some embodiments may also include storing the determined configuration settings in a tangible computer readable memory associated with the first hearing prosthesis.

21 Claims, 4 Drawing Sheets

SYSTEMS, METHODS, AND ARTICLE OF MANUFACTURE FOR CONFIGURING A HEARING PROSTHESIS

BACKGROUND

Various types of hearing prostheses may provide persons with different types of hearing loss with the ability to perceive sound. Hearing loss may be conductive, sensorineural, or some combination of both conductive and sensorineural hearing loss.

Conductive hearing loss typically results from a dysfunction in any of the mechanisms that ordinarily conduct sound waves through the outer ear, the eardrum, or the bones of the middle ear. Persons with some forms of conductive hearing loss may benefit from hearing prostheses such as acoustic hearing aids, bone anchored hearing aids, and direct acoustic cochlear stimulation devices.

Sensorineural hearing loss typically results from a dysfunction in the inner ear, including the cochlea where sound vibrations are converted into neural signals, or any other part of the ear or auditory nerve, that may process the neural signals. Persons with some forms of sensorineural hearing loss may benefit from hearing prostheses such as cochlear implants and auditory brain stem implants.

Depending on the severity of the sensorineural hearing loss, some persons may benefit from using a hybrid prosthesis in one ear (e.g., a combined acoustic hearing aid with a cochlear implant). Persons may also benefit from using different prostheses in each ear (e.g., an acoustic hearing aid in one ear and a cochlear implant in the opposite ear). Using separate hearing prostheses may sometimes be referred to as bimodal hearing because the prosthesis recipient is hearing in two modes, e.g., acoustically and electrically in the case where the two prostheses include an acoustic hearing aid and a cochlear implant.

The effectiveness of a hearing prosthesis depends not only on the design of the prosthesis itself but also on how well the prosthesis is configured for or "fitted" to a prosthesis recipient. The fitting of the prosthesis, sometimes also referred to as "programming" or "mapping," creates a set of configuration settings and other data that define the specific characteristics of the signals (acoustic, mechanical, or electrical) delivered to the relevant portions of the person's outer ear, middle ear, inner ear, or auditory nerve. This configuration information is sometimes referred to as the recipient's "program" or "MAP."

SUMMARY

The present application discloses systems, methods, and articles of manufacture for configuring a first hearing prosthesis based on configuration settings associated with a second hearing prosthesis. The first and/or second hearing prostheses may be a cochlear implant, a bone anchored hearing aid, a direct acoustic cochlear stimulation device, an auditory brain stem implant, or an acoustic hearing aid. In some embodiments, the first hearing prosthesis may be a cochlear implant and the second hearing prosthesis may be an acoustic hearing aid.

Some embodiments may include determining configuration settings for a first hearing prosthesis based on configuration data associated with a second hearing prosthesis, and storing the determined configuration settings in a tangible computer readable memory associated with the first hearing prosthesis. Some embodiments may additionally include acquiring the configuration data associated with the second hearing prosthesis from a computer readable memory associated with the second hearing prosthesis. Further embodiments may additionally include configuring the first hearing prosthesis based on the determined configuration settings.

In some embodiments, the configuration data associated with the second hearing prosthesis may include data corresponding to whether a gain associated with at least one signal generated by the second hearing prosthesis is within a predefined range of a corresponding target gain.

In some embodiments, determining the configuration settings for the first hearing prosthesis may include determining a first acoustic operating range associated with the first hearing prosthesis. In such embodiments, the first acoustic operating range may include at least one acoustic frequency where a signal generated by the second hearing prosthesis corresponding to the at least one acoustic frequency fails to achieve a target signal level. For embodiments where the first hearing prosthesis includes a sound processor configured to convert acoustic sounds to output signals, determining configuration settings for the first hearing prosthesis may include determining sound processor settings for the first hearing prosthesis. The sound processor settings may include data related to the acoustic operating range.

The first acoustic operating range associated with the first hearing prosthesis may be different than a second acoustic operating rage associated with the second hearing prosthesis in some embodiments. However, in other embodiments, the first acoustic operating range and the second acoustic operating range may be substantially the same. In some embodiments, the first acoustic operating range may at least partially overlap the second acoustic operating range. In still other embodiments, the first acoustic operating range may not overlap the second acoustic operating range.

In some embodiments, the first hearing prosthesis may be configured for use with one of a prosthesis recipient's ears while the second hearing prosthesis may be configured for use with the prosthesis recipient's opposite, or contralateral, ear. However, in other embodiments, the first and second hearing prostheses may be configured for use in the same ear of the prosthesis recipient.

For embodiments where the first hearing prosthesis may be a cochlear implant and the second hearing prosthesis may be an acoustic hearing aid, the configuration settings for the cochlear implant may correspond to frequency allocation table settings for the cochlear implant, and the configuration data for the acoustic hearing aid may correspond to gain settings and/or performance characteristics of the acoustic hearing aid.

The first hearing prosthesis in some embodiments may be a hybrid prosthesis for use with one of a prosthesis recipient's ears. The hybrid prosthesis may comprise a cochlear implant component and an acoustic hearing aid component. In such embodiments, determining configuration settings for the first hearing prosthesis may include determining an acoustic operating range associated with the cochlear implant component. The determined acoustic operating range may include at least one acoustic frequency corresponding to a signal generated by the second hearing prosthesis that fails to meet a target signal level.

DETAILED DESCRIPTION

The following detailed description describes various features and functions of the disclosed systems, methods, and articles of manufacture with reference to the accompanying figures. In the figures, similar symbols typically identify similar components, unless context dictates otherwise. The illustrative system, method, and article of manufacture embodiments described herein are not meant to be limiting. Certain aspects of the disclosed embodiments can be arranged and combined in a wide variety of different configurations, all of which are contemplated herein.

Certain aspects of the disclosed systems, methods, and articles of manufacture may be described herein with reference to cochlear implant and acoustic hearing aid embodiments. However, the disclosed systems, methods, and articles of manufacture are not so limited. Many of the disclosed features and functions described with respect to the cochlear implant and acoustic hearing aid embodiments may be equally applicable to other embodiments that may include other types of hearing prostheses, such as, for example, bone anchored hearing aids or types of vibration-based hearing prostheses configured to transmit sound via direct vibration of teeth or other cranial or facial bones, direct acoustic cochlear stimulation devices, auditory brain stem implants, or any other type of hearing prosthesis that may be configured to convert received acoustic signals within a defined acoustic frequency range to one or more output signals, where the output signals are based on the received acoustic signals.

Hearing Prostheses

Figure 1:
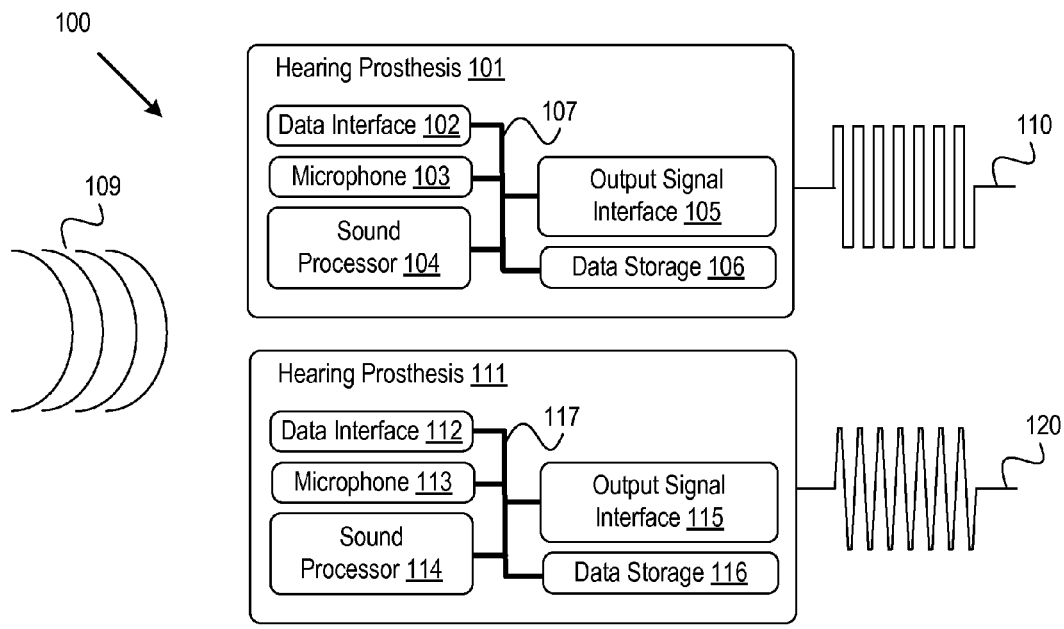
FIG. 1 shows one example of two hearing prostheses configured according to some embodiments of the disclosed systems, methods, and articles of manufacture.

FIG. 1 shows one example configuration 100 of a first hearing prosthesis 101 and a second hearing prosthesis 111 configured according to some embodiments of the disclosed systems, methods, and articles of manufacture. The first hearing prosthesis 101 and/or the second hearing prosthesis 111 may be a cochlear implant, an acoustic hearing aid, a bone anchored hearing aid or other vibration-based hearing prosthesis, a direct acoustic stimulation device, an auditory brain stem implant, or any other type of hearing prosthesis configured to aid a prosthesis recipient in hearing sound.

The first hearing prosthesis 101 may include a data interface 102, a microphone 103, a sound processor 104, an output signal interface 105, and data storage 106, all of which may be connected directly or indirectly via circuitry 107. Similarly, the second hearing prosthesis 111 may include a data interface 112, a microphone 113, a sound processor 114, an output signal interface 115, and data storage 116, all of which may be connected directly or indirectly via circuitry 117. In some embodiments, the first hearing prosthesis 101 or the second hearing prosthesis 111 may have additional or fewer components than the prostheses shown in FIG. 1. Additionally, the components may be arranged differently than shown in FIG. 1. For example, depending on the type and design of the hearing prostheses, the illustrated components may be enclosed within a single operational unit or distributed across multiple operational units (e.g., and external unit, an internal unit, etc.). Similarly, in some embodiments, the first hearing prosthesis 101 may additionally include one or more processors (not shown) configured to determine configuration settings for its sound processor 104 based on configuration data associated with the second hearing prosthesis 111.

In embodiments where the first hearing prosthesis 101 is a cochlear implant, the microphone 103 may be configured to receive acoustic signals 109, and the sound processor 104 may be configured to analyze and encode the acoustic signals 109 into electrical stimulation signals 110 for application to an implant recipient's cochlea via an output signal interface 105 that may include an array of electrodes. In embodiments where the second hearing prosthesis 111 is an acoustic hearing aid, the microphone 113 may be configured to receive acoustic signals 109, and the sound processor 114 may be configured to analyze and encode the acoustic signals 109 into acoustic output signals 120 for applying to a recipient's ear via an output signal interface 105 comprising a speaker.

For embodiments where the first hearing prosthesis 101 or the second hearing prosthesis 111 is a bone anchored hearing aid (BAHA) or other vibration-based hearing prosthesis, the microphone 103 or 113 may be configured to receive acoustic signals 109, and the sound processor 104 or 114 may be configured to analyze and encode the acoustic signals 109 into mechanical vibration output signals 110 or 120 for applying to the recipient's skull (or teeth or other cranial or facial bone) via output signal interface 105 or 115 that may include a mechanism to transmit sound via direct bone vibrations. Similarly, for embodiments where the first hearing prosthesis 101 or the second hearing prosthesis 111 is a direct acoustic cochlear stimulation (DACS) device, the microphone 103 or 113 may be configured to analyze and encode the acoustic signals 109 into mechanical vibration output signals 110 or 120 for applying to the DACS recipient's inner ear via output signal interface 105 or 115 that may include a mechanism to transmit sound via direct vibration. Finally, for embodiments where the first hearing prosthesis 101 or the second hearing prosthesis 111 is an auditory brain stem implant, the microphone 103 or 113 may be configured to analyze and encode the acoustic signals 109 into electrical stimulation output signals 110 or 120 for applying to the auditory brain stem implant recipient's auditory nerve via output signal interface 105 or 115 that may include one or more electrodes.

Hearing Prosthesis Fitting System

The effectiveness of a hearing prosthesis 101 or 111 may depend not only on the design and capabilities of the device, but also on how well the device is configured for or "fitted" to a recipient. The fitting of a hearing prosthesis 101 or 111, sometimes referred to as "programming" or "mapping," may include creating a set of configuration settings and other data that defines how the sound processor 104, 114 of the prosthesis 101, 111 analyzes and converts acoustic signals 109 received by the microphone 103, 113 to output signals 110, 120 transmitted to the prosthesis recipient via the output signal interface 105,115. This configuration information is sometimes referred to as the recipient's "program" or "MAP." The recipient's "program" or "MAP" may be loaded into the prosthesis 101, 111 via the data interface 102, 112 and stored in the data storage 106, 116 of the hearing prosthesis.

Figure 2:
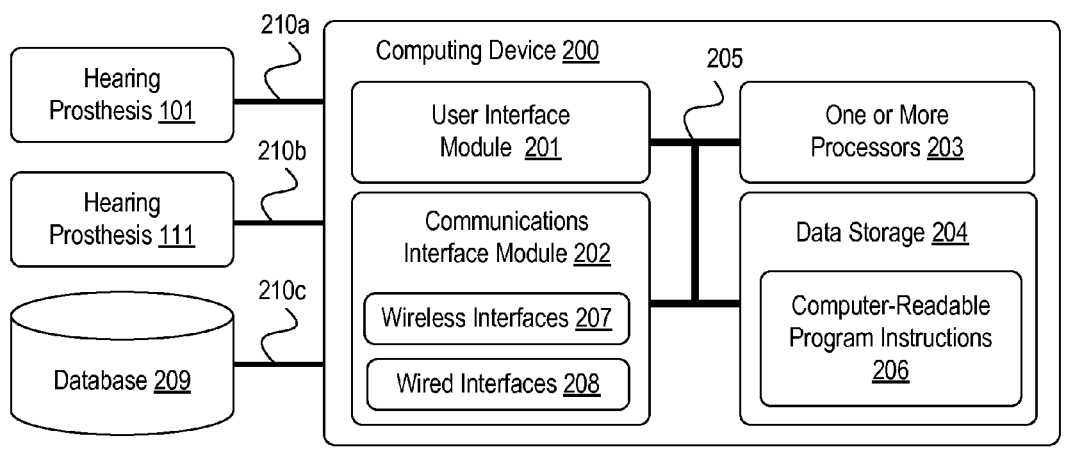
FIG. 2 shows an example of a fitting system configured according to some embodiments of the disclosed systems, methods, and articles of manufacture.

FIG. 2 shows a block diagram of an example of a computing device 200 that may be configured to execute fitting software for a particular hearing prosthesis and to load configuration settings to the data storage 106, 116 of a hearing prosthesis 101, 111 via the prosthesis' data interface 102, 112. The computing device 200 may include a user interface module 201, a communications interface module 202, one or more processors 203, and data storage 204, all of which may be linked together via a system bus or other connection circuitry 205.

The user interface module 201 may be configured to send data to and/or receive data from external user input/output devices such as a keyboard, a keypad, a touch screen, a computer mouse, a track ball, a joystick, and/or other similar devices, now known or later developed. The user interface module 201 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 201 may also be configured to generate audible output(s), such as a speaker, speaker jack, audio output port, audio output device, earphones, and/or other similar devices, now known or later developed. In some embodiments, the user interface module 201 may include or be communicatively coupled to an LCD or similar type of touch screen. The touch screen may be configured to display a user interface and/or to receive commands from a user.

The communications interface module 202 may include one or more wireless interfaces 207 and/or wired interfaces 208 that may be configurable to communicate with a hearing prosthesis 101, 111 via a communications connection 210a, 210b, to a database 209 via communications connection 210c, or to other computing devices (not shown). The wireless interfaces 207 may include one or more wireless transceivers, such as a Bluetooth transceiver, a Wi-Fi transceiver, a WiMAX transceiver, and/or other similar type of wireless transceiver configurable to communicate via a wireless protocol. The wired interfaces 208 may include one or more wired transceivers, such as an Ethernet transceiver, a Universal Serial Bus (USB) transceiver, or similar transceiver configurable to communicate via a twisted pair wire, a coaxial cable, a fiber-optic link or a similar physical connection.

The one or more processors 203 may include one or more general purpose processors (e.g., microprocessors manufactured by Intel or Advanced Micro Devices) and/or one or more special purpose processors (e.g., digital signal processors, application specific integrated circuits, etc.). The one or more processors 203 may be configured to execute computer-readable program instructions 206 that may be contained in the data storage 204 and/or other instructions based on algorithms described herein.

The data storage 204 may include one or more computer-readable storage media that can be read or accessed by at least one of the processors 203. The one or more computer-readable storage media may include volatile and/or non-volatile storage components, such as optical, magnetic, organic or other memory or disc storage, which can be integrated in whole or in part with at least one of the processors 203. In some embodiments, the data storage 204 may be implemented using a single physical device (e.g., one optical, magnetic, organic or other memory or disc storage unit), while in other embodiments, the data storage 204 may be implemented using two or more physical devices.

The data storage 204 may include computer-readable program instructions 206 and perhaps additional data. In some embodiments, the data storage 204 may additionally include storage that may be required to perform at least part of the herein-described methods and algorithms and/or at least part of the functionality of the systems described herein.

FIG. 2 shows the computing device 200 connected both the first hearing prosthesis 101 and the second hearing prosthesis 111 for illustration purposes. In some embodiments, computing device 200 may include software for configuring both the first hearing prosthesis 101 and the second hearing prosthesis 111. But in other embodiments, the first hearing prosthesis 101 and the second hearing prosthesis 111 may be configured by different computing devices.

Hearing Prosthesis Configuration Settings

In some embodiments, the one or more processors 203 of the computing device 200 may be configured to execute fitting software program instructions for determining one or more configuration settings for the first hearing prosthesis 101 based on configuration data associated with a second hearing prosthesis 111. The computing device 200 may also be configured to store the determined configuration settings in a tangible computer readable memory associated with the first hearing prosthesis 101. The tangible computer readable memory may include the data storage 204 of the computing device 200, the data storage 106 of the first hearing prosthesis 101, and/or database 209.

In other embodiments, one or more processors (not shown) of the first hearing prosthesis 101 may be configured to execute fitting software program instructions for determining one or more of the configuration settings for the first hearing prosthesis 101 based on configuration data associated with the second hearing prosthesis 111. The first hearing prosthesis 101 may also be configured to store the determined configuration settings in a tangible computer readable memory, such as the data storage 106 of the first hearing prosthesis 101, the data storage 204 of the computing device 200, and/or database 209.

In some embodiments, the configuration data associated with the second hearing prosthesis 111 may be stored in a tangible computer readable memory associated with the second hearing prosthesis 111, such as, for example, the data storage 204 of the computing device 200, the data storage 116 of the second hearing prosthesis 111, or an external database 209. In embodiments where the second hearing prosthesis 111 is an acoustic hearing aid, the configuration data associated with the second hearing prosthesis 111 may be in (i) a format proprietary to the second hearing prosthesis 111 manufacturer, (ii) a Hearing Instrument Manufactures' Software Association (HIMSA) Noah database compatible format or other industry standard format, or (iii) some combination of proprietary and industry standard formats.

In some embodiments, as part of determining the one or more configuration settings for the first hearing prosthesis 101, one or processors (associated with computing device 200 or with the first hearing prosthesis 101) may be configured to determine an acoustic operating range associated with the first hearing prosthesis based on the configuration data associated with the second hearing prosthesis 111. The acoustic operating range for the first hearing prosthesis 101 may correspond to a particular range of acoustic frequencies (within the acoustic signal 109) on which the output signals 110 may be based. For example, the microphone 103 may detect acoustic signals 109 over a wide acoustic frequency range (e.g., 20 Hz-18 kHz), but the sound processor 104 may be configured to generate output signals 110 based on the sounds between 250 Hz and 8 kHz (or some other frequency range or ranges). For example, in embodiments where a prosthesis recipient may wear the first hearing prosthesis 101 in one ear and the second hearing prosthesis 111 in the opposite ear, the acoustic operating range of the first hearing prosthesis 101 may be based at least in part on the configuration settings and/or the performance of the second hearing prosthesis 111. In such an arrangement, the acoustic operating range of the first hearing prosthesis 101 may be selected to accommodate shortcomings in the performance of the second hearing prosthesis 111 or possibly to enhance the recipient's total hearing experience.

Figure 3:
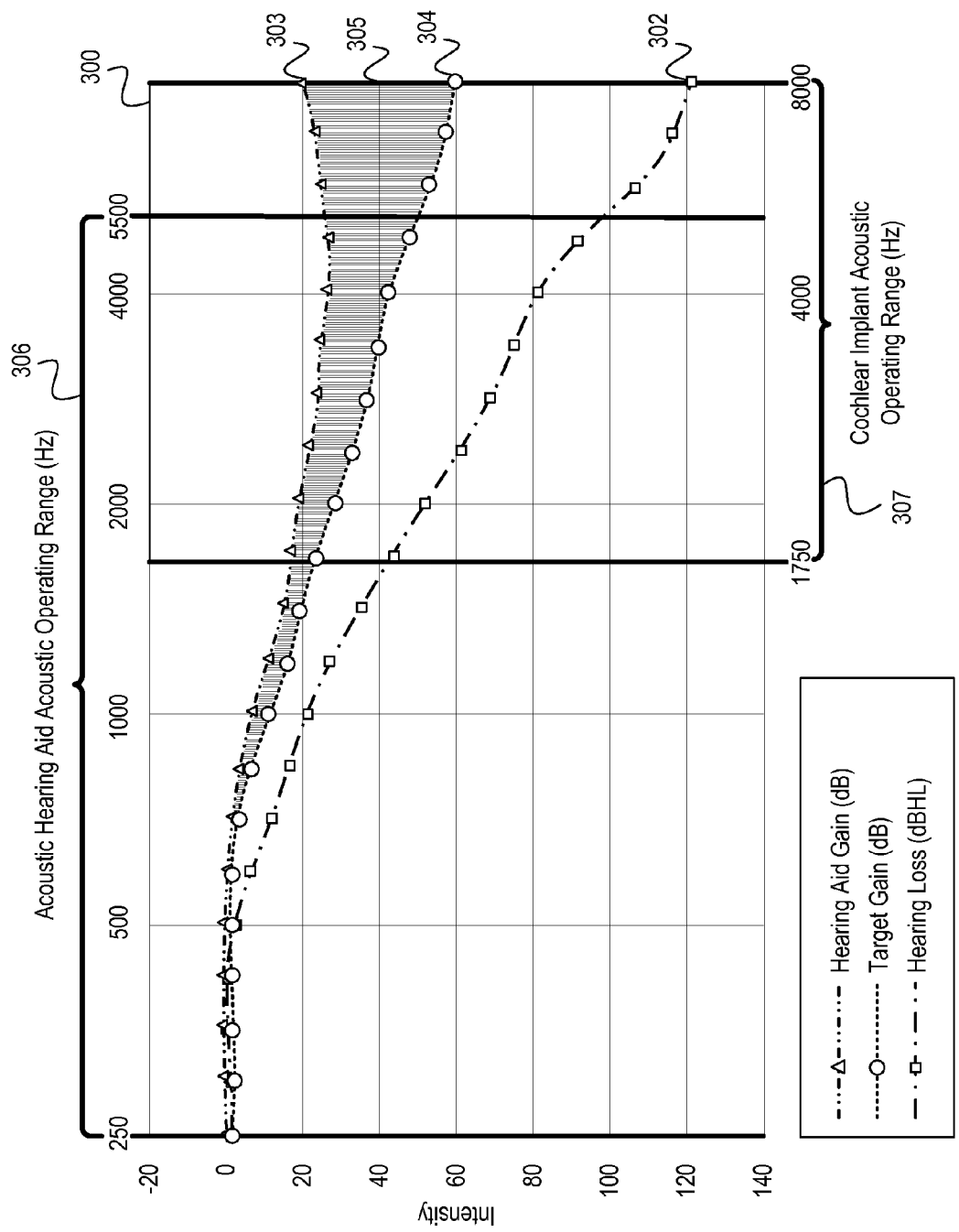
FIG. 3 illustrates certain configuration settings associated with a first and second hearing prosthesis according to some embodiments of the disclosed systems, methods, and articles of manufacture.

FIG. 3 illustrates certain configuration settings associated with a first and second hearing prosthesis according to some embodiments of the disclosed systems, methods, and articles of manufacture. In the embodiment shown in FIG. 3, the first hearing prosthesis may be a cochlear implant and the second prosthesis may be an acoustic hearing aid. However, other combinations of hearing prostheses could be used with the disclosed systems, methods, and articles of manufacture.

In the audiogram 300, trace 302 shows a prosthesis recipient's hearing loss in decibels as a function of acoustic frequency between 250 Hz and 8 kHz. Trace 304 shows the target gain as a function of acoustic frequency that would be required to restore the prosthesis recipient's hearing to a desired hearing level, and trace 303 shows the actual gain of the acoustic hearing aid as a function of acoustic frequency. The shaded region 305 shows the area where the actual gain 303 of the acoustic hearing aid cannot achieve the target gain 304 required to restore the prosthesis recipient's hearing to the desired hearing level. In some embodiments, the data shown in FIG. 3 related to the recipient's hearing loss 302, the target gain 304, and the acoustic hearing aid gain 303 may be stored in computer readable media associated with the acoustic hearing aid. For example, the configuration data may be stored in the data storage 116 (FIG. 1) of the acoustic hearing aid, data storage 204 of a computing device 200 (FIG. 2), or a database 209 (FIG. 2) configured to store the configuration data of the acoustic hearing aid.

There could be many different reasons why the actual gain 303 of the acoustic hearing aid might not achieve the target gain 304 at some acoustic frequencies. For example, the acoustic hearing aid may cause undesirable feedback when generating output signals 120 (FIG. 1) at certain acoustic frequencies. Sometimes, the prosthesis recipient's hearing loss is so profound that the acoustic hearing aid may simply be unable to provide sufficient gain to achieve the target gain 304 at particular acoustic frequencies. In such situations, the acoustic hearing aid recipient may benefit from an additional hearing prosthesis such as a cochlear implant or other hearing prosthesis. The additional hearing prosthesis could be used in the same ear as the acoustic hearing aid or in the recipient's opposite, or contralateral, ear.

In addition to showing the recipient's hearing loss 302, the target gain 304, and the actual acoustic hearing aid gain 303, FIG. 3 also shows the acoustic operating range 306 of the acoustic hearing aid and the acoustic operating range 307 of the cochlear implant. In some embodiments, determining the acoustic operating range 307 of the cochlear implant based on the configuration data associated with acoustic hearing aid may include determining an acoustic operating range 307 for the cochlear implant so that the overlap of the binaural frequency range (i.e., the overlap of the acoustic operating ranges 306 and 307) may enable the recipient's brain to combine and compare the cochlear implant's output signals 110 (FIG. 1) and the acoustic hearing aid's output signals 111 (FIG. 1) for experiencing a desired range of acoustic signals 109 (FIG. 1).

In the example shown in FIG. 3, the acoustic operating range 306 of the acoustic hearing aid is configured for 250 Hz to 5500 Hz, and the acoustic operating range 307 of the cochlear implant is configured for 1750 Hz to 8000 Hz. The combined acoustic operating range of the acoustic hearing aid and the cochlear implant is configured for 250 Hz to 8000 Hz, which roughly corresponds to the acoustic range of most human speech. The ranges shown in FIG. 3 are for illustration purposes, and other ranges could be used with the disclosed systems, methods, and articles of manufacture.

For example, in alternative embodiments, the acoustic operating range 306 of the acoustic hearing aid may be the same (or substantially the same) as the acoustic operating range 307 of the cochlear implant. In still further embodiments, the acoustic operating range 306 of the acoustic hearing aid may not overlap the acoustic operating range 307 of the cochlear implant. Similarly, the acoustic operating range 306 of the acoustic hearing aid need not be a continuous frequency range, and the acoustic operating range 307 of the cochlear implant need not be a continuous frequency range. In some embodiments, the acoustic operating range 307 of the cochlear implant may be selected based on how well the actual gain 303 of the acoustic hearing aid meets the target gain 304 from between about 250 Hz and 2000 Hz or within some other defined range.

As described with respect to FIGS. 1 and 2, some embodiments of the disclosed systems, methods, and articles of manufacture may include determining the acoustic operating range of the first hearing prosthesis based on configuration data associated with the second hearing prosthesis. For embodiments like the one shown in FIG. 3 where the first hearing prosthesis may be a cochlear implant and the second hearing prosthesis may be an acoustic hearing aid, the acoustic operating range of the cochlear implant may be selected to include at least one frequency where the gain 303 generated by the acoustic hearing aid is less than a configurable or predetermined threshold offset from the target gain 304. In some embodiments, the acoustic operating range of the cochlear implant may be selected to include at least one acoustic frequency where the gain 303 generated by the acoustic hearing aid fails to achieve the target gain 304.

In some embodiments, configuring the acoustic operating range 307 of the cochlear implant may include determining settings for the cochlear implant's frequency allocation table (FAT). As described previously, the output interface 105 (FIG. 1) of a cochlear implant may include an array of electrodes configured to deliver electric output signals 110 (FIG. 1) to a cochlear implant recipient's cochlea. The array of electrodes may be organized into channels, where individual channels may include one or more active electrodes and one or more reference electrodes. The cochlear implant's FAT may define the acoustic frequency range (frequency bandwidth) assigned to individual channels of the cochlear implant. For example, in embodiments where the cochlear implant may have 22 active channels (i.e., groupings of active and reference electrodes), the acoustic operating range of the cochlear implant may be divided into multiple acoustic frequency ranges across the acoustic operating range, where each acoustic frequency range may correspond to an individual channel including one or more active electrodes and one or more reference electrodes.

The audiogram 300 illustrates example configuration settings for an acoustic hearing aid used in one of a recipient's ears and a cochlear implant used in the recipient's opposite ear. However, the example configuration settings illustrated in the audiogram 300 may be equally applicable to hybrid prostheses, such as a hybrid prosthesis including an acoustic hearing aid portion and a cochlear implant portion where the prosthesis can be configured to deliver acoustic signals 120 (FIG. 1) and electric signals 110 (FIG. 1) to the same ear of the recipient. In such an embodiment, a computing device 200 (FIG. 2) (or alternatively the hybrid prosthesis itself) may be configured to determine an acoustic operating range 307

(FIG. 3) associated with the cochlear implant portion based on the configuration settings of the acoustic hearing aid portion.

For example, in such a hybrid prosthesis embodiment, the acoustic operating range 306 corresponding to the acoustic hearing aid portion may be configured to not overlap the acoustic operating range 307 of the cochlear implant portion. In operation, the acoustic operating range 307 of the cochlear implant portion of the hybrid prosthesis may be based on how well the gain 303 of the acoustic hearing aid portion meets a target gain 304 (or a threshold associated with the target gain 304) designed to accommodate the recipient's hearing loss 302.

In some hybrid prosthesis embodiments, the acoustic operating ranges 306 and 307 of the acoustic hearing aid and cochlear implant portions may be based on configuration settings associated with a hearing prosthesis configured for use with the recipient's opposite ear. In such embodiments, the acoustic operating range 307 of the cochlear implant portion of the hybrid prosthesis may be based on the configuration settings of (i) the acoustic hearing aid portion of the hybrid prosthesis and/or (ii) a separate hearing prosthesis configured for use in the recipient's opposite ear, such as another acoustic hearing aid or other prosthesis. In operation, the acoustic operating range 307 of the cochlear implant portion of the hybrid prosthesis may be based on (i) how well the gain 303 of the acoustic hearing aid portion meets a target gain 304 (or a threshold associated with the target gain 304) designed to accommodate the recipient's hearing loss 302 and/or (ii) how well the gain (not shown) of the separate hearing prosthesis configured for use in the recipient's opposite ear meets its corresponding target gain (or threshold associated therewith) (not shown).

Although hybrid prosthesis examples have been described with respect to embodiments where the hybrid prosthesis has a cochlear implant component and an acoustic hearing aid component, other types of hybrid prostheses may be used with the disclosed systems, methods, and articles of manufacture as well. For example, other types of hybrid prostheses may include various combinations of a cochlear implant, a bone anchored hearing aid or other vibration-based hearing prosthesis, a direct acoustic cochlear stimulation device, an auditory brain stem implant, or an acoustic hearing aid.

Example Methods for Determining Hearing Prosthesis Settings

Figure 4:
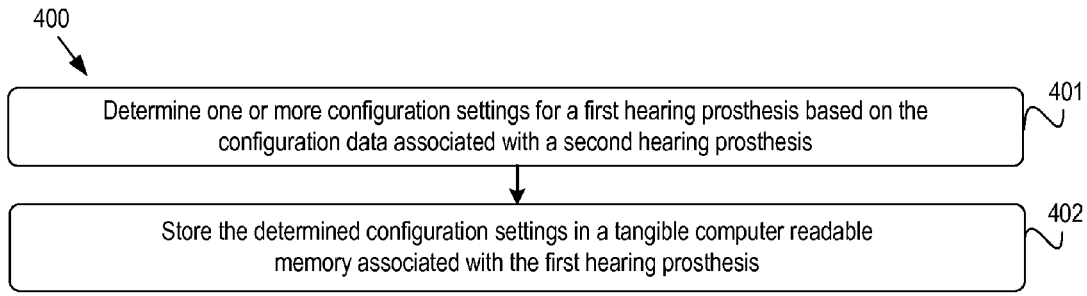
FIG. 4 shows one example method for determining configuration settings for a hearing prosthesis according to some embodiments.

FIG. 4 shows an example method 400 for determining configuration settings for a hearing prosthesis according to some embodiments.

Method 400 begins at method block 401 where one or more configuration settings for a first hearing prosthesis may be determined based on configuration data associated with a second hearing prosthesis. In some embodiments, determining the one or more configuration settings for the first hearing prosthesis may include determining an acoustic operating range associated with the first hearing prosthesis. In some embodiments, the acoustic operating range may include at least one acoustic frequency where a signal generated by the second hearing prosthesis corresponding to the at least one acoustic frequency fails to achieve a target signal level (or a threshold setting associated with the target signal level). In further embodiments, determining the one or more configuration settings for the first hearing prosthesis may include determining an acoustic operating range associated with the first hearing prosthesis. In some embodiments, the acoustic operating range may include at least one acoustic frequency where a configured gain of the second hearing prosthesis corresponding to the at least one acoustic frequency fails to achieve a target gain (or a threshold setting associated with the target gain).

In some embodiments, the acoustic operating range of the first hearing prosthesis may at least partially overlap an acoustic operating range associated with the second hearing prosthesis. In other embodiments, the acoustic operating range of the first hearing prosthesis may not overlap the acoustic operating range of the second hearing prosthesis. In still other embodiments, the acoustic operating range of the first hearing prosthesis may be substantially the same as the acoustic operating range of the second hearing prosthesis.

Method 400 may continue at method block 402 where the determined configuration settings may be stored in a computer readable memory associated with the first hearing prosthesis. In some embodiments, the computer readable memory may be similar to the data storage 106 (FIG. 1) of the first hearing prosthesis 101 (FIG. 1), the data storage 204 (FIG. 2) of the computing device 200 (FIG. 2), or other computer readable memory (not shown) that may be associated with the first hearing prosthesis.

Some embodiments of method 400 may additionally include acquiring the configuration data associated with the second hearing prosthesis from a computer readable memory associated with the second hearing prosthesis. The computer readable memory associated with the second hearing prosthesis may be the data storage 116 (FIG. 1) associated with the second hearing prosthesis, the data storage 204 (FIG. 2) of the computing device 200 (FIG. 2), or a separate database 209 (FIG. 2) associated with the second hearing prosthesis. The configuration data associated with the second hearing prosthesis may be stored, in some embodiments, in (i) a format proprietary to the second hearing prosthesis 111 manufacturer, (ii) a Hearing Instrument Manufactures' Software Association (HIMSA) Noah database compatible format or other industry standard format, or (iii) some combination of proprietary and industry standard formats.

Further embodiments of method 400 may also additionally include configuring the first hearing prosthesis based on the one or more configuration settings determined in method block 401. Configuring the first hearing prosthesis may include loading the determined configuration settings of method block 401 into data storage 106 (FIG. 1) of the first hearing prosthesis 101 (FIG. 1) via data interface 102 (FIG. 1).

In some embodiments of method 400, the first hearing prosthesis may be a cochlear implant, a bone anchored hearing aid, a direct acoustic cochlear stimulation device, an auditory brain stem implant, or an acoustic hearing aid. Similarly, in some embodiments of method 400, the second hearing prosthesis may be a cochlear implant, a bone anchored hearing aid or other vibration-based hearing prosthesis, a direct acoustic cochlear stimulation device, an auditory brain stem implant, or an acoustic hearing aid. In some embodiments, the first hearing prosthesis may be a cochlear implant and the second hearing prosthesis may be an acoustic hearing aid.

In some embodiments of method 400, the first hearing prosthesis may be configured for use with one of a prosthesis recipient's ears, and the second hearing prosthesis may be configured for use with the prosthesis recipient's opposite, or contralateral, ear. In other embodiments of method 400, the first hearing prosthesis may correspond to a first component of a hybrid prosthesis that includes multiple hearing prosthesis components (e.g., a cochlear implant component and an acoustic hearing aid component), and the second hearing prosthesis may correspond to (i) the second component of the hybrid prosthesis and/or (ii) a separate hearing prosthesis configured for use in the recipient's opposite, or contralateral, ear.

Algorithms for Determining a Hearing Prosthesis Acoustic Operating Range

Figure 5:
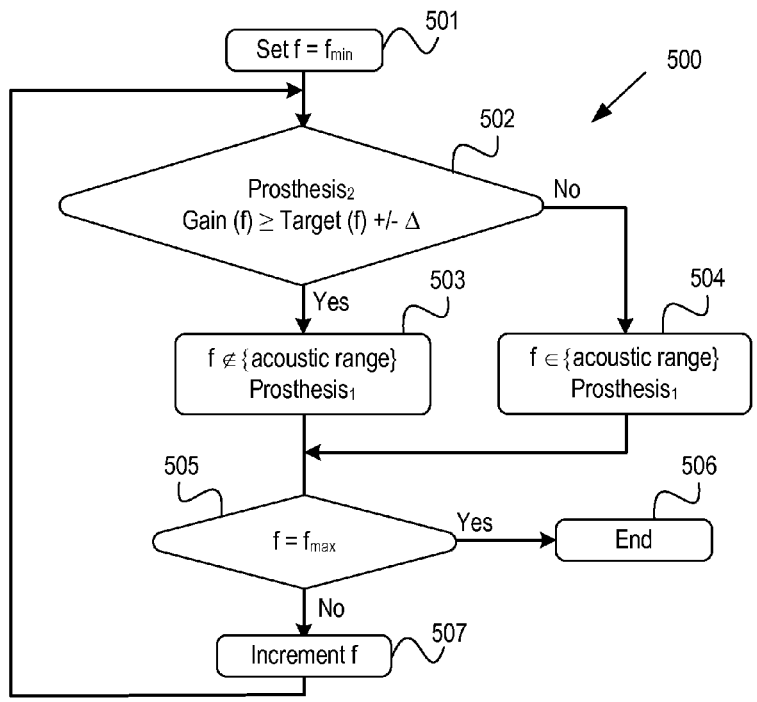
FIG. 5 shows an example algorithm for determining an acoustic operating range associated with a hearing prosthesis according to some embodiments.

FIG. 5 shows an example algorithm 500 for determining an acoustic operating range associated with a hearing prosthesis according to some embodiments. In algorithm 500, the acoustic operating range of a first hearing prosthesis, Prosthesis$_1$, may be determined based on configuration settings associated with a second hearing prosthesis, Prosthesis$_2$.

Algorithm 500 may begin at block 501 where a current frequency, f, is set to a minimum frequency, $f_{min}$. In some embodiments, the minimum frequency, $f_{min}$, may correspond to the lowest acoustic frequency of a desired hearing range, e.g., 250 Hz to 8000 Hz shown in FIG. 3. However, other values for the minimum frequency, $f_{min}$, and other ranges for the desired hearing range may be used as well. The desired hearing range may correspond to a range of acoustic frequencies within acoustic signal 109 (FIG. 1).

At block 502, the second hearing prosthesis', Prosthesis$_2$, gain at frequency f, Gain(f), may be compared to a target gain at frequency f, Target(f). In some embodiments, the second hearing prosthesis', Prosthesis$_2$, gain at frequency f, Gain(f), may be compared to an offset or threshold (+/−Δ) relative to the target gain at frequency f, Target(f).

In some embodiments, if the gain for the second prosthesis at frequency f, Gain(f), is greater than (or greater than or equal to in some embodiments) the target gain at frequency f, Target(f), then at block 503, frequency f may not be included in the set of frequencies corresponding to the acoustic operating range of the first hearing prosthesis, Prosthesis$_1$. But if the gain for the second prosthesis at frequency f, Gain(f), is less than (or less than or equal to in some embodiments) the target gain at frequency f, Target(f), then at block 504, frequency f may be included in the set of frequencies corresponding to the acoustic operating range of the first hearing prosthesis, Prosthesis$_1$.

In alternative embodiments, if the gain for the second prosthesis at frequency f, Gain(f), is greater than (or greater than or equal to in some embodiments) a defined threshold offset (+/−Δ) relative to the target gain at frequency f, Target(f), then at block 503, frequency f may not be included in the set of frequencies corresponding to the acoustic operating range of the first hearing prosthesis. But if the gain for the second prosthesis at frequency f, Gain(f), is less than (or less than or equal to in some embodiments) the defined threshold offset (+/−Δ) relative to the target gain at frequency f, Target(f), then at block 504, frequency f may be included in the set of frequencies corresponding to the acoustic operating range of the first hearing prosthesis.

At block 505, the current frequency, f, may be compared to a maximum frequency, $f_{max}$. In some embodiments, the maximum frequency, $f_{max}$, may correspond to the highest acoustic frequency of a desired hearing range, e.g., 250 Hz to 8000 Hz as shown in the example illustrated in FIG. 3. However, other values for the maximum frequency, $f_{max}$, and other ranges for the desired hearing range may be used as well. If the current frequency, f, is equal to the maximum frequency, $f_{max}$, then the algorithm 500 may end at block 506. But if the current frequency, f, is not equal to the maximum frequency, $f_{max}$, then the current frequency, f, may be incremented at block 507. The algorithm 500 may then return to block 502.

In some embodiments, the disclosed features and functions of the devices shown in FIGS. 1-3 and the methods and algorithms shown and described in FIGS. 4-5 may be implemented as computer program instructions encoded on a computer readable media in a machine-readable format.

Figure 6:
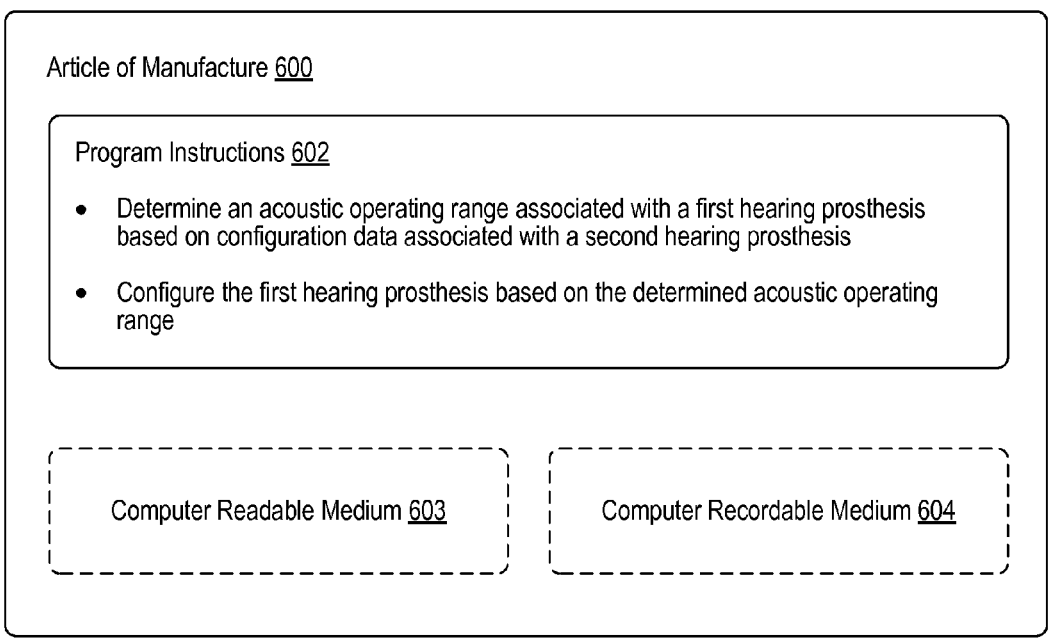
FIG. 6 shows an article of manufacture including computer readable media according to some embodiments.

FIG. 6 shows an article of manufacture including computer readable media according to some embodiments. FIG. 6 shows a schematic illustrating a conceptual partial view of an example article of manufacture 600 that may include computer program instructions 602 for executing a computer process on a computing device, arranged according to at least some embodiments described herein.

In some examples, the article of manufacture 600 may include a computer-readable medium 603, such as, but not limited to, a hard disk drive, a Compact Disc (CD), a Digital Video Disk (DVD), a digital tape, memory, etc. In some implementations, the article of manufacture 600 may include a computer recordable medium 604, such as, but not limited to, memory, read/write (R/W) CDs, R/W DVDs, etc.

The one or more programming instructions 602 may be, for example, computer executable and/or logic implemented instructions. In some embodiments, a computing device such as the computing device 200 shown and described in FIG. 2 may be configured to perform various operations, functions, or actions to implement the features and functionality of the disclosed systems and methods based on the programming instructions 602. In still other embodiments, one or more processors (not shown) associated with the first hearing prosthesis 101, alone or in combination with the sound processor 104 of the first hearing prosthesis 101, may be configured to perform various operations, functions, or actions to implement the features and functionality of the disclosed systems and methods based on the programming instructions 602.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
determining one or more configuration settings for a first hearing prosthesis based on configuration data associated with a second hearing prosthesis, wherein determining the one or more configuration settings comprises (i) making a determination, based on the configuration data associated with the second hearing prosthesis, of whether a signal generated at an acoustic frequency by the second hearing prosthesis achieves a target signal level, and (ii) determining the one or more configuration settings based on the determination; and
instructing the first hearing prosthesis to store the determined configuration settings in a tangible computer readable memory associated with the first hearing prosthesis,
wherein determining the one or more configuration settings comprises omitting the acoustic frequency from a first acoustic operating range associated with the first hearing prosthesis in response to the determination being that the signal generated at the acoustic frequency by the second hearing prosthesis achieves the target signal level.

2. The method of claim 1, further comprising:
acquiring the configuration data associated with the second hearing prosthesis from a computer readable memory associated with the second hearing prosthesis.

3. The method of claim 1, wherein determining the one or more configuration settings based on the determination comprises:

including the acoustic frequency in the first acoustic operating range associated with the first hearing prosthesis in response to the determination being that the signal generated at the acoustic frequency by the second hearing prosthesis fails to achieve a target signal level; and determining one or more configuration settings for each acoustic frequency included in the first acoustic operating range.

4. The method of claim 1, wherein the first acoustic operating range associated with the first hearing prosthesis does not overlap a second acoustic operating range associated with the second hearing prosthesis.

5. The method of claim 1, wherein the first hearing prosthesis is configured for use with a first ear of a prosthesis recipient, and wherein the second hearing prosthesis is configured for use with a second ear of the prosthesis recipient.

6. The method of claim 1, wherein the first and second hearing prostheses are configured for use with a first ear of a prosthesis recipient.

7. The method of claim 1, wherein the first hearing prosthesis is one of a cochlear implant, a bone anchored hearing aid, a direct acoustic cochlear stimulation device, an auditory brain stem implant, or an acoustic hearing aid, and wherein the second hearing prosthesis is an acoustic hearing aid.

8. The method of claim 1, wherein the first hearing prosthesis is a cochlear implant and the second hearing prosthesis is an acoustic hearing aid, wherein the one or more configuration settings for the first hearing prosthesis correspond to one or more frequency allocation table settings for the cochlear implant, and wherein the configuration data associated with the second hearing prosthesis corresponds to gain characteristics of the acoustic hearing aid.

9. The method of claim 1, wherein the first hearing prosthesis is a hybrid prosthesis comprising a cochlear implant component and an acoustic hearing aid component, wherein the second hearing prosthesis is an acoustic hearing aid, and wherein determining the one or more configuration settings for the first hearing prosthesis based on configuration data associated with the second hearing prosthesis comprises:

determining an acoustic operating range associated with the cochlear implant component of the first hearing prosthesis, wherein the acoustic operating range includes at least one acoustic frequency corresponding to a signal generated by the second hearing prosthesis that fails to meet a target signal level.

10. An article of manufacture including non-transitory computer-readable media with instructions stored thereon, the instructions comprising:

instructions for determining an acoustic operating range associated with a first hearing prosthesis based on configuration data associated with a second hearing prosthesis, wherein the instructions include, for each of one or more acoustic frequencies:

(i) making a determination of whether a signal generated at the acoustic frequency by the second hearing prosthesis achieves a target signal level, wherein the determination is based on the configuration data associated with the second hearing prosthesis; and (ii) determining, based on the determination, whether to include the acoustic frequency in the acoustic operating range, wherein, for each of the one or more acoustic frequencies, determining whether to include the acoustic frequency in the acoustic operating range comprises omitting the acoustic frequency from the acoustic operating range in response to the determination being that the signal generated at the acoustic frequency by the second hearing prosthesis achieves the target signal level.

11. The article of manufacture of claim 10, further comprising:

instructions for acquiring the configuration data associated with the second hearing prosthesis from a computer readable memory associated with the second hearing prosthesis; and instructions for configuring the first hearing prosthesis based on the determined acoustic operating range.

12. The article of manufacture of claim 10, wherein determining, based on the determination, whether to include the acoustic frequency in the acoustic operating range comprises including the acoustic frequency in the acoustic operating range in response to the determination being that the signal generated at the acoustic frequency by the second hearing prosthesis fails to achieve the target signal level.

13. The article of manufacture of claim 10, wherein the first hearing prosthesis is one of a cochlear implant, a bone anchored hearing aid, a direct acoustic cochlear stimulation device, an auditory brain stem implant, or an acoustic hearing aid, and wherein the second hearing prosthesis is a cochlear implant, a bone anchored hearing aid, a direct acoustic cochlear stimulation device, an auditory brain stem implant, or an acoustic hearing aid.

14. The article of manufacture of claim 10, wherein the first hearing prosthesis is a hybrid prosthesis comprising a cochlear implant component and an acoustic hearing aid component, wherein the second hearing prosthesis is an acoustic hearing aid, and wherein the instructions for determining an acoustic operating range associated with the first hearing prosthesis include instructions for determining the acoustic operating range associated with the cochlear implant component of the hybrid prosthesis.

15. A system comprising:

one or more processors configured to determine sound processor settings for a first hearing prosthesis based on configuration data associated with a second hearing prosthesis, wherein the sound processor settings include information indicative of one or more frequency channels included in an acoustic operating range of the first hearing prosthesis, and wherein, to determine the sound processor settings, the one or more processors are further configured to:

(i) make a determination, based on the configuration data associated with the second hearing prosthesis, of whether a gain of a signal generated at a frequency by the second hearing prosthesis meets a target gain, wherein the frequency and the target gain correspond to a frequency channel, and (ii) determine, based on the determination, whether to include the frequency channel in the acoustic operating range, wherein, in response to the determination being that the signal generated at the frequency by the second hearing prosthesis meets the target gain, the one or more processors are configured to omit the frequency channel from the acoustic operating range; and computer-readable memory configured to store the determined sound processor settings.

16. The system of claim 15, further comprising:

one or more communications interfaces configured to (i) receive the configuration data associated with the second hearing prosthesis from a computer-readable memory associated with the second hearing prosthesis and (ii) send the determined sound processor settings to the first hearing prosthesis.

17. The system of claim 15, wherein the first hearing prosthesis is one of a cochlear implant, a bone anchored hearing aid, a direct acoustic cochlear stimulation device, an auditory brain stem implant, or an acoustic hearing aid, and wherein the second hearing prosthesis is an acoustic hearing aid.

18. The system of claim 15, wherein the first hearing prosthesis is a hybrid prosthesis comprising a cochlear implant component and an acoustic hearing aid component, and wherein the second hearing prosthesis is an acoustic hearing aid.

19. The system of claim 15, wherein the first hearing prosthesis includes the one or more processors and the computer-readable memory.

20. The system of claim 15, wherein the one or more processors are components of a hearing prosthesis fitting system associated with the first hearing prosthesis.

21. The system of claim 15, wherein the one or more processors are further configured to include the frequency channel in the acoustic operating range in response to the determination being that the signal generated at the frequency by the second hearing prosthesis fails to meet the target gain.

* * * * *